(12) United States Patent
Samuel et al.

(10) Patent No.: US 11,434,481 B2
(45) Date of Patent: Sep. 6, 2022

(54) RAPID NON-DESTRUCTIVE GENETIC MATERIAL COLLECTION

(71) Applicant: University of Utah Research Foundation, Salt Lake City, UT (US)

(72) Inventors: Raheel Samuel, Salt Lake City, UT (US); Christopher J. Lambert, Salt Lake City, UT (US); Bruce K. Gale, Salt Lake City, UT (US); Joshua L. Bonkowsky, Salt Lake City, UT (US); Briana Freshner, Salt Lake City, UT (US); Tak Chi Arlen Chung, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 200 days.

(21) Appl. No.: 16/628,622

(22) PCT Filed: Jul. 3, 2018

(86) PCT No.: PCT/US2018/040799
§ 371 (c)(1),
(2) Date: Jan. 3, 2020

(87) PCT Pub. No.: WO2019/010229
PCT Pub. Date: Jan. 10, 2019

(65) Prior Publication Data
US 2021/0139885 A1    May 13, 2021

Related U.S. Application Data

(60) Provisional application No. 62/618,936, filed on Jan. 18, 2018, provisional application No. 62/528,339, filed on Jul. 3, 2017.

(51) Int. Cl.
C12N 15/10 (2006.01)
A01K 67/00 (2006.01)
B01L 3/00 (2006.01)

(52) U.S. Cl.
CPC .......... *C12N 15/1003* (2013.01); *A01K 67/00* (2013.01); *B01L 3/508* (2013.01);
(Continued)

(58) Field of Classification Search
CPC ..... C12N 15/1003; A01K 67/00; B01L 3/508; B01L 2200/141; B01L 2300/0893;
(Continued)

(56) References Cited

U.S. PATENT DOCUMENTS 9,096,823 B1    8/2015  Branch et al.
2001/0031467 A1   10/2001 Dapprich et al.
(Continued)

FOREIGN PATENT DOCUMENTS

| CN | 106754301 A | 5/2017 |
| EP | 3184624 A1 | 6/2017 |
| WO | WO 2015/104358 A1 | 7/2015 |

OTHER PUBLICATIONS

Samuel et al. ("Microfluidic-aided genotyping of zebrafish in the first 48 h with 100% viability." Biomedical microdevices 17.2 (2015): 1-7) (Year: 2015).*

(Continued)

*Primary Examiner* — Jennifer Wecker
*Assistant Examiner* — Oyeleye Alexander Alabi
(74) *Attorney, Agent, or Firm* — Thorpe North and Western LLP (57) ABSTRACT

A device for rapid non-destructive genetic material collection can include a multi-reservoir array (202) and a movement mechanism. The multi-reservoir array (202) can include multiple reservoirs (204). A plurality of the multiple
(Continued)

reservoirs (204) can include an abrasive surface (210) capable of retaining a source of genetic material in a liquid carrier. The abrasive surface (210) has a roughness. The movement mechanism can be operable to move the multi-reservoir array (202) in an oscillating motion sufficient to create relative movement between the abrasive surface (210) and the source of the genetic material in order to remove a portion of genetic material from the source of the genetic material without destroying the source of the genetic material or the portion of the genetic material that is removed.

21 Claims, 7 Drawing Sheets (52) U.S. Cl.
CPC . *B01L 2200/141* (2013.01); *B01L 2300/0893* (2013.01); *B01L 2300/16* (2013.01); *B01L 2400/0433* (2013.01)

(58) Field of Classification Search
CPC ......... B01L 2300/16; B01L 2400/0433; B01L 2200/0647; B01L 3/5085; C12Q 1/6806
See application file for complete search history.

(56) References Cited

U.S. PATENT DOCUMENTS

| | | |
|---|---|---|
| 2003/0124505 A1 | 7/2003 | Jain et al. |
| 2006/0121603 A1 | 6/2006 | Yuan et al. |
| 2012/0190126 A1 | 7/2012 | Eshoo et al. |
| 2014/0272971 A1 | 9/2014 | Higgins |
| 2016/0083687 A1 | 3/2016 | Sanders et al. |
| 2016/0333298 A1 | 11/2016 | Hung et al. |
| 2016/0354783 A1 | 12/2016 | Lapham et al. |

OTHER PUBLICATIONS

Branch et al.; "Intelligent Front-end Sample Preparation Tool using Acoustic Streaming." Sandia National Laboratories; Published Sep. 1, 2009; 59 Pages.

Chen et al.; "Multicolor cell barcoding technology for long-term surveillance of epithelial regeneration in Zebrafish." Dev Cell; Elsevier; Mar. 21, 2016; vol. 36. No. 6; pp. 668-680.

Gale et al.; "Microfluidic Devices for Rapid and Sensitive Identification of Organisms." 36$^{th}$ Annual International Conference of the IEEE Engineering in Medicine and Biology Society, EMBC; 2014; pp. 774-777.

Hwang et al.; "Miniaturized bead-beating device to automate full DNA sample preparation processes for Gram-positive bacteria." Lab on a Chip; Royal Society of Chemistry; Sep. 14, 2011; vol. 11, Issue 21; pp. 3649-3655.

Hwang et al.; "Solid Phase DNA Extraction with a Flexible Bead-Packed Microfluidic Device to Detect Methicillin Resistant *Staphylococcus aureus* in Nasal Swabs." Analytical Chemistry; ACS Publications; Aug. 21, 2012; pp. 7912-7918.

PCT Application No. PCT/US18/40799 Filing date Jul. 3, 2018; Raheel Samuel; International Search Report; dated Dec. 6, 2018; 15 Pages.

Samuel et al.; "Microfluidic-aided genotyping of Zebrafish in the first 48 h with 100% viability." Biomed Microdevices; 2015; vol. 17, No. 2; p. 43 (pp. 1-7).

\* cited by examiner

FIG. 7C eif2B5 CRISPR alleles

| Allele# | amino acid sequence (aa 28-32) |
|---|---|
| wt | EEEQPLQAVLVAQ... |
| zcA2 | EEEQP------LVAQ... |
| zcA3 | EEENPRWWPTVST... |
| zcC3 | EEEQPL--AVLVAQ... |
| zcB8 | EEEQ------AVLVAQ... |

RAPID NON-DESTRUCTIVE GENETIC MATERIAL COLLECTION

RELATED APPLICATIONS

This application claims priority to U.S. Provisional Application No. 62/618,936 filed on Jan. 18, 2018 and U.S. Provisional Application No. 62/528,339 filed on Jul. 3, 2017, which are incorporated herein by reference.

GOVERNMENT INTEREST

This invention was made with government support under Grant Number R43 OD023027 awarded by the National Institutes of Health. The government has certain rights in the invention.

BACKGROUND

Zebrafish (*Danio rerio*) are a small, yet powerful, vertebrate model organism for biomedical research. The zebrafish body plan, organs, and genes can be conserved in other vertebrates, including humans. Additionally, zebrafish can exhibit rapid development, have transparent to semi-transparent embryos, and can have a large numbers of offspring. Accordingly, zebrafish can be utilized in determining genetic and biochemical pathways, identifying basic biological mechanisms, testing genetic variants, pre-clinical drug discovery testing, and modeling human diseases.

While zebrafish can be utilized in Clustered Regularly Interspaced Short Palindromic Repeats (CRISPR) mutagenesis; their capability for genotyping can be a time, labor, and training intensive process. Current genotyping techniques can include growing embryos to adult age (two to three months) and manually clipping their fins. Fin clipping and genotyping 96 zebrafish can be a four to six hour process, in addition to the two to three months wait. Alternatively, zebrafish embryos or larvae can be sacrificed and genotyped. If individual organisms need to be distinctly genotyped this process can be even more laborious and can involve additional testing. Further, the ability for large-scale screens can be limited by the absence of automated genotyping tools for live animals, which can lead to limitations on drug and mutant screens and an inability to capitalize on the potential for identifying new therapies and bio-pharmacological pathways.

SUMMARY

A device for rapid non-destructive genetic material collection and method for rapid non-destructive genetic material collection are presented herein. The device can include a multi-reservoir array and a movement mechanism. The multi-reservoir array can include multiple reservoirs. A plurality of the multiple reservoirs can include an abrasive surface capable of generating and or retaining a source of genetic material in a liquid carrier and the abrasive surface can have a roughness. The movement mechanism can be operable to move the multi-reservoir array in an oscillating motion sufficient to create relative movement between the abrasive surface and the source of the genetic material in order to remove a portion of genetic material from the source of the genetic material without destroying the source of the genetic material or the portion of the genetic material that is removed.

Further presented herein, is a method of rapid non-destructive genetic material collection. The method can include, retaining a living source of genetic material within multiple reservoirs that can have an abrasive surface therein; moving the abrasive surface relative to the living source of the genetic material in a manner that can remove genetic material from the source of the genetic material without destroying the genetic material and the living source of the genetic material to form a recovered genetic material; and collecting the recovered genetic material.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

In describing and claiming the present invention, the following terminology will be used.

The singular forms "a," "an," and "the" include plural referents unless the context clearly dictates otherwise. Thus, for example, reference to "a reservoir" includes reference to one or more of such materials and reference to "subjecting" refers to one or more such steps.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 1%, and most often less than 0.5%, and in some cases less than 0.01%.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, "non-destructive genetic material collection," and "without destroying the source of the genetic material" refers to a material collection process that retains the viability of the source of the genetic material without apparent effects on body morphology or motor behavior and with the capability of future reproduction by the source of the genetic material at a survivability rate of at least 80%, and in some cases at least 90%.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the phrase "at least one of" is intended to be synonymous with "one or more of" For example, "at least one of A, B and C" explicitly includes only A, only B, only C, and combinations of each.

As used herein, the phrase "a plurality of" is intended to be synonymous with "two or more of" For example, a plurality of A, B, and C explicitly includes A and B; B and C; A and C; or A, B, and C.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Presented herein is a device that can be automated to rapidly, accurately, and efficiently genotype live embryos without destroying the viability of the live embryos. The device can also be utilized to perform high throughput genotyping and raising of knock-in mutants or other mutants of interest at an early stage of development rather than waiting until maturity, and can sort homozygous, heterozygous, and wild-type embryos for a given genotype or mutation while the animals are alive. The device can reduce the time, effort, money necessary to generate and screen mutants rapidly. For example, genotyping of live zebrafish embryos 72 hours post-fertilization (hpf) can be performed with these systems.

Figure 1:
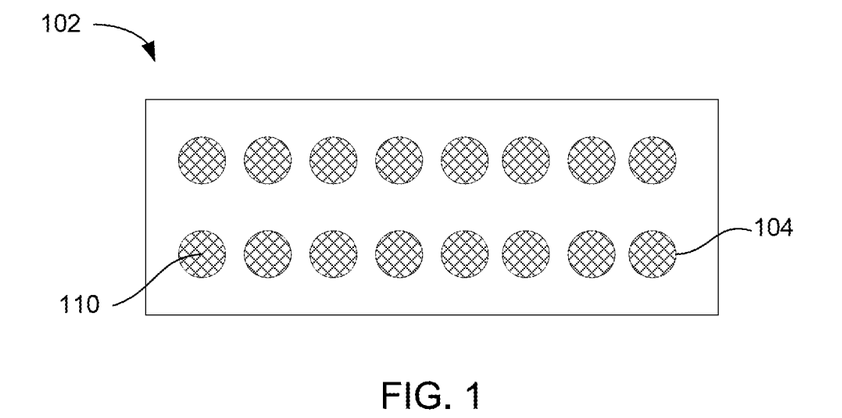
FIG. 1 graphically depicts a multi-reservoir array in accordance with an example of the present disclosure.
Figure 2:
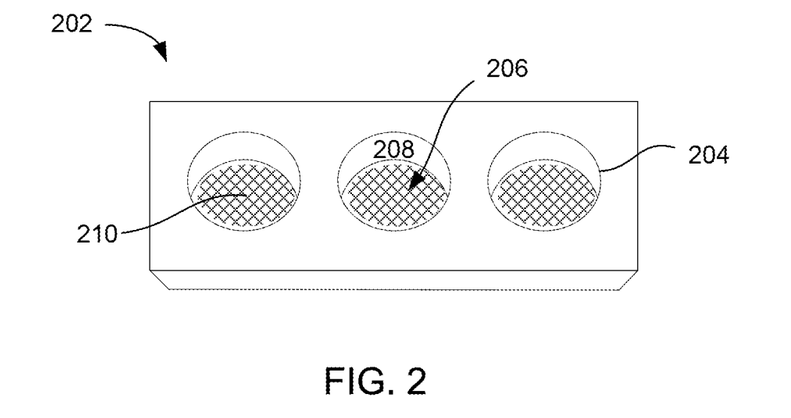
FIG. 2 graphically depicts a multi-reservoir array having cylindrical reservoirs in accordance with an example of the present disclosure.

The device for rapid non-destructive genetic material collection can include a substrate capable of retaining a living source of genetic material in a liquid carrier and including an abrasive surface and a movement mechanism. The device can be mechanically moved (e.g. vibrated, oscillated, or shaken) by the movement mechanism in order to create friction between the abrasive surface and the source of genetic material thereby causing genetic material to be removed from a surface of the source of the genetic material. In one embodiment, the substrate can include a multi-reservoir array 102, including a plurality of reservoirs 104, having an abrasive surface 110, as shown in FIG. 1. Referring to FIG. 2, the reservoirs 204 of the multi-reservoir array 202 can include a reservoir bottom 206, reservoir side wall 208, and abrasive surface 210.

In further detail, the reservoirs of the multi-reservoir array can be wells, channels, chambers, open top droplet, platform, or a combination thereof. In one example, the reservoirs can be wells. The wells can be any type of well utilized in microarrays. In one example, the reservoirs can be chimney wells, rounded wells, flat bottom wells, round bottom wells, conical bottom wells (such as v-shaped or u-shaped), cuboid, or any combination thereof. In one example, the reservoirs can be cylindrical channels or chambers. In another example, the cylindrical chambers can be a 20 µL chamber molded in PDMS that can be bonded to a glass slide having a roughened surface. Alternatively, the reservoirs can be dedicated locations on a platform. In this case surface tension and adhesion forces retain fluid samples in place during processing.

The roughened surface can be etched in the glass slide or adhered thereto. In some examples, the channels or chambers can be pressurized and/or can include pneumatic microvalves to drive fluid flow to an extraction chamber.

In yet another example, the multi-reservoir array can include an open top droplet system. For example, an open top droplet system can be a slide with hydrophobic tape having holes that can form a side wall of the reservoirs. Non-limiting examples of suitable hydrophobic tape can include polyimide tape (e.g. KAPTON), TEFLON, silicone, and the like. The hydrophobic tape in some examples can have a thickness that can range from 10 microns to 200 microns, from 25 microns to 175 microns, or from 50 microns to 150 microns. In yet another example, the open top droplet system can be a slide with indentations less than 200 microns deep that form the reservoirs. In a further example, an open top droplet system can be formed using a structure less than 200 microns thick and adhering that structure to a substrate such as a glass slide or a thermal plastic. Additionally, hydrophobic materials including sprays (e.g. silicone, Teflon) as well as other treatment methods for generating hydrophobic surfaces (e.g. plasma, surface patterning, topographical modification, laser) can be used.

The reservoirs on the substrate can vary in number, shape, and/or size. None of these parameters are particularly limited and can be chosen based on the application of the device. In some examples, the multi-reservoir array can have 3, 16, 24, 36, 48, 64, or 96 reservoirs. The shape of the reservoirs can include circle, oval, square, rectangular, linear, or polygonal. The size of the reservoirs can most often range from 1 mm to 10 mm, from 2 mm to 8 mm, or from 3 mm to 7 mm, although reservoirs up to 1 cm, and even 3 cm can be useful in some cases. In one example, the multi-reservoir array can include up to 96 reservoirs that can be circular, and can have a diameter ranging from 2 mm to 8 mm in size with a depth from 0.5 mm to 4 mm. For the example of wells, depths can vary from about 0.1 mm to about 1 cm, and often from 0.2 mm to 10 mm.

The multi-reservoir array can be composed of a variety of materials. For example, the multi-reservoir array can be composed of polystyrene, polypropylene, polydimethylsiloxane, polyethylene, glass, ceramic, nylon, silicon, acrylic, metal or any combination thereof. In one example, the multi-reservoir array can include molded polydimethylsiloxane (PDMS) forming the reservoir side wall which can be adhered to a slide that forms the reservoir bottom. The slide can be composed of glass, acrylic, or the like. The abrasive surface can be any surface having a roughness operable to remove genetic material from the source without destroying the genetic material or the source of the genetic material.

In one embodiment, the abrasive surface can include a member selected from the group consisting of a roughened portion of the multi-reservoir array, an abrasive material attached to an interior surface of the multiple reservoirs, and a combination thereof. In some examples, the roughened surface can be located along a bottom and/or a sidewall of the multiple reservoirs. For example, the roughened surface, as indicated by the hatched lines, can be located along the bottom 206 of the reservoirs 204 as shown in FIG. 2. In some examples, the multi-reservoir array can be a slide having a roughened surface and a molded article can be adhered thereto that forms the reservoir side wall of the multi-reservoir array. In other examples, the roughened surface can be a separate article that can be adhered to portions of the multi-reservoir array.

The roughness (Ra) and Waviness (Wa) of the abrasive surface can vary. For example, the abrasive surface can have a roughness and waviness ranging from 1 μm to 100 μm, from 10 μm to 90 μm, from 15 μm to 85 μm, or from 25 μm to 45 μm. The roughness (Ra) and Waviness (Wa) as measured herein refers to the roughness average and waviness average of a surface as measured by microscopic peaks and valleys. Surface roughness can be determined using optical or contact-based surface profilers.

The abrasive surface can be formed in any suitable manner. In one example, one or more walls of the reservoirs can be roughened. This can be accomplished by etching, ablation, deposition, or the like. Variations in etching and ablation time can result in varied surface roughness (e.g. longer etching time tends to produce higher roughness). In another example, alone or in combination, a loose abrasive material can be fixedly attached to interior surfaces of the multiple reservoirs. This may be accomplished by gluing, brazing, melting, or the like.

The roughness and waviness can be a factor in determining the appropriate mechanical movement mechanism, the duration of the movement, and the amplitude of the movement; as the type of movement, the amount of friction produced by the movement, and the speed of the movement, in addition to the roughness, can all be factors that contribute to the removal of the genetic material. As a general guideline, duration of the movement can be from 1 min to 30 min, and often from 5 min to 10 min. Similarly, the velocity of movement can also contribute to aggressiveness of the process and thus survivability. As a general guideline, velocity can range from 0.1 m/s to 1 m/s, and most often from 0.3 m/s to 0.8 m/s. For example, a roughness Ra 2 can be used with a 0.5 m/s movement mechanism, for 5 minutes of time. A rougher surface will require less time and/or strength to remove cells than a smoother surface. Similarly, a higher amplitude can result in collection at lower times while also risking lower survivability.

Figure 3:
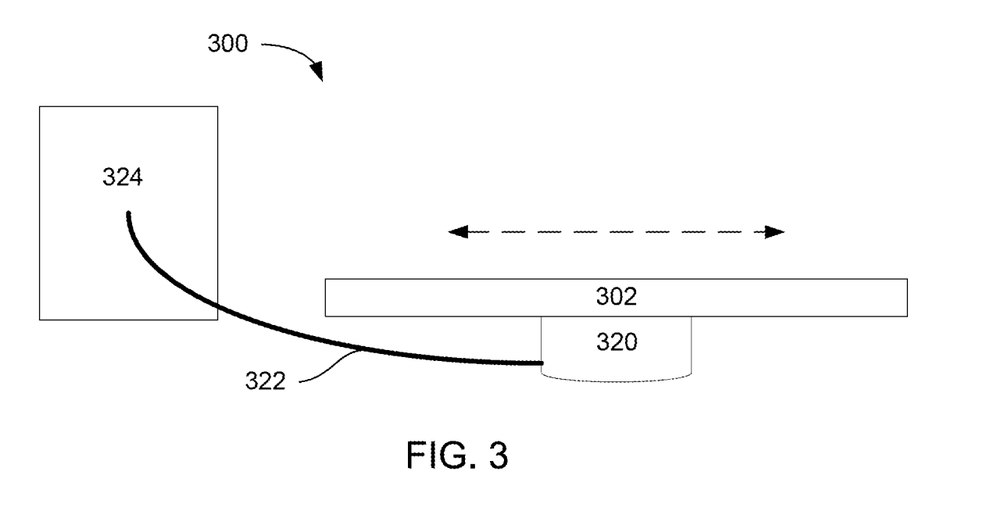
FIG. 3 graphically depicts a device for rapid non-destructive genetic material collection in accordance with an example of the present disclosure.

The movement mechanism can be operable to move the multi-reservoir array in an oscillating motion that can be sufficient to create relative movement between the abrasive surface and the source of the genetic material in order to remove the genetic material from the source without destroying the genetic material or the source of the genetic material. Non-limiting examples of suitable movement mechanisms can include a shaker plate, an orbital shaker, a linear shaker, a rocking shaker, a gyratory rocker, a microplate mixer, a vibration motor, a coin vibration motor, a reciprocating rack, and any combination thereof. The location of the movement mechanism can vary. In some instances, the movement mechanism 320 can be located along a bottom surface of the multi-reservoir array 302 as shown in FIG. 3. Also shown are the control 324 for the movement mechanism and the electrical connector 322 between the movement mechanism and the control. In yet other examples, the movement mechanism can be located at or near a lateral edge of the multi-reservoir array. In one example, the multi-reservoir array can be loaded onto a modified commercial shaker plate which orbited in a 3 mm diameter circular planar motion at a specified rpm.

In some examples, the device can include quality enhancing features. For example, the multi-reservoir array can be disposable. A disposable multi-reservoir array can prevent DNA contamination/cross-talk. In another example, the multi-reservoir array can include a bactericide and/or viricide coating in order to reduce contaminate growth. In yet another example, the multi-reservoir array can include a sealing film. In yet another example, the device can include a timer and can optionally include an automatic shut-off after a specified period of time. Thus in some cases, the timer can be operably connected to disconnect the movement mechanism.

Figure 4:
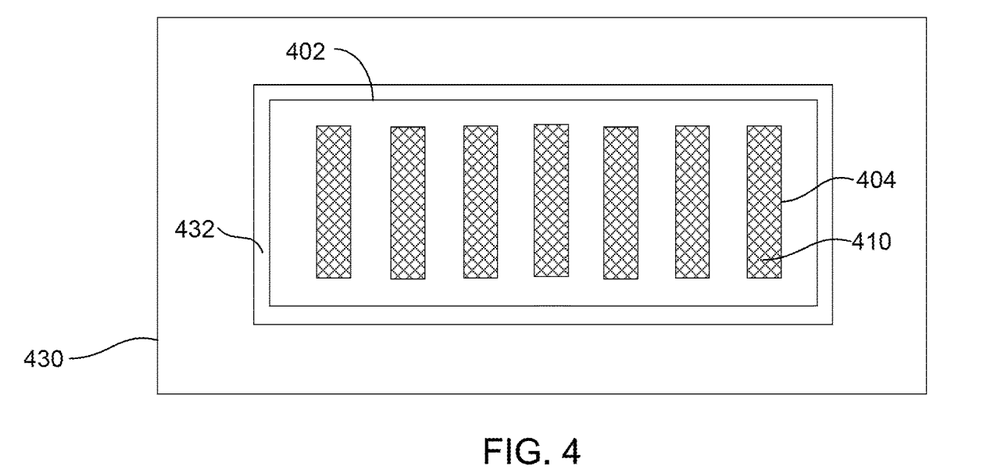
FIG. 4 graphically depicts a multi-reservoir array in a base unit in accordance with an example of the present disclosure.

In a further example, the device can include a base plate upon which the multi-reservoir array can be placed. The base plate can be used to provide a larger surface for attachment to the movement mechanism. The base plate can include a holder or receptacle for the multi-reservoir array. The holder can be any mechanism capable of securing the multi-reservoir array to the base plate. For example, the holder can be a recessed area of the base plate, a raised portion of the base plate, clips, grips, combinations thereof, and the like. In some examples, the base plate 430 can include a recessed area 432 that the multi-reservoir array 402 can rest in as shown in FIG. 4. Also shown are a plurality of reservoirs 404 having an abrasive surface 410.

Figure 5:
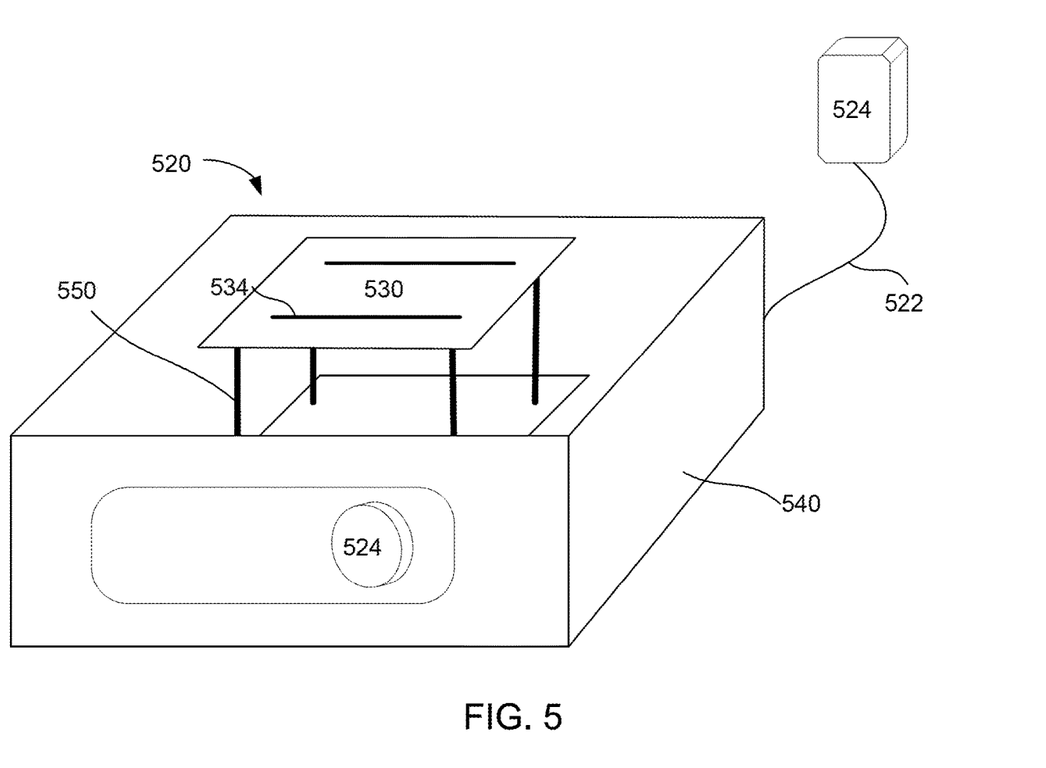
FIG. 5 graphically depicts a movement mechanism and base unit in accordance with an example of the present disclosure.

In some examples, the base plate can be oriented within a suitable housing and secured to a raised system that can be placed on or interior of a movement mechanism. For example, as shown in FIG. 5, the movement mechanism 520 which includes control 524 and electrical connectors 522 and 526, can provide a location that a base plate 530 can be placed upon. In 530 the holder of the base plate is raised portions 534 of the base plate which interface with a bottom outer surface of the multi-reservoir array. In some examples an evaporation limiting cover, a displacement dampening mechanism, and or vibration feedback system are utilized. In some cases, the interface can include latches, detents, clips, retention frames, interference friction fit, or other mechanisms to secure the multi-reservoir array to the base plate during use. The base plate 530 can also be secured to a foundation or device housing 540 via compression springs 550 to permit planar movement. Alternatively, a mechanism acts to suspend the base plate while allowing for freedom of movement as affected by the displacement generator (e.g. vibration motor).

Optionally, the system can further include a sorting unit which allows segregation of embryos from one another, chorionic fluid, collected DNA, debris, and waste fluid. Thus, the sorting unit can be used before introduction into the device or after operation of the device. Alternatively, the sorting unit can be used both before and after the process. Such sorting can result in collected samples which are manually placed in diagnostic or other units. However, in one aspect, the sorting unit can be fluidly and operatively connected to the material collection device to allow for automated transfer of materials into the multi-reservoir array.

Figure 6:
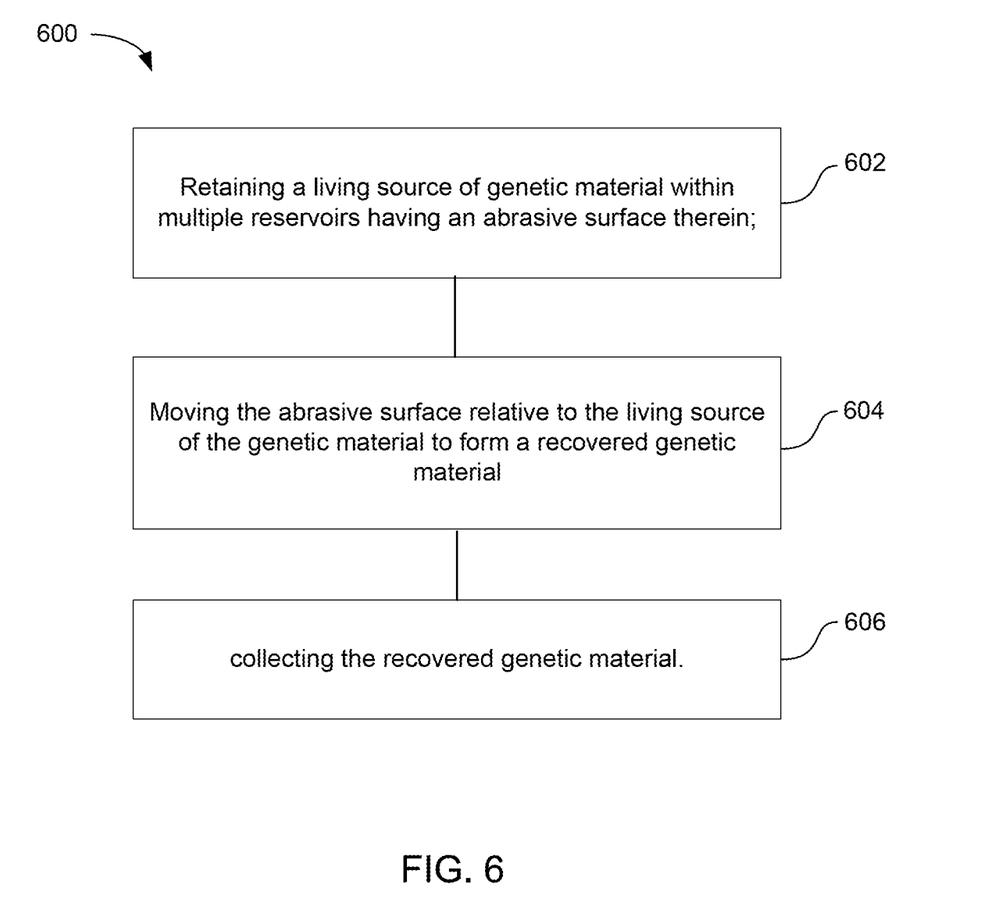
FIG. 6 a method of rapid non-destructive genetic material collection in accordance with an example of the present disclosure.

Further presented herein, is a method of rapid non-destructive genetic material collection 600 as generally outlined in FIG. 6. The method can include retaining 602 a living source of genetic material within multiple reservoirs having an abrasive surface therein, moving 604 the abrasive surface relative to the living source of the genetic material in a manner that can remove genetic material from the source of the genetic material without destroying the genetic material and the living source of the genetic material to form a recovered genetic material; and collecting 606 the recovered genetic material. In one example, the multiple reservoirs can be a multi-reservoir array as described above. Thus, using microfluidic harmonic oscillation of the living source on an abrasive surface can result in recovery of genetic material with a high survivability.

The source of genetic material can be a plant or animal source. In some examples, the source can be a 24-96 hour post fertilization embryo. In one example, the source of genetic material can be a 72 hour post fertilization embryo. In another example, the source of genetic material can be a tissue sample. In other examples, the source of genetic material can be larvae. In further examples, the source of genetic material can be an aquatic vertebrate. In one example, the source of the genetic material can be a zebrafish (*Danio rerio*), Japanese rice fish (medaka), trout, fruit fly (*drosophila*), nematode, round worms (*C. elegans*), frog, or an African clawed frog (*Xenopus*). In other examples, the source of genetic material can be zebrafish. In some examples, the living source of genetic material can be one of the above sources which has had exposure to a mutagen. In another example, the living source is subjected to CRISPR mutagenesis. The resulting embryos can be screened and subjected to further next-generation sequencing and genotyping. For example, recovered genetic material can be amplified by PCR and used for sequencing, gel electrophoresis, high resolution melt analysis, or the like as described herein.

In one example, the step of retaining the living source of genetic material can include loading the reservoirs with the living source of the genetic material retained in 10-20 µL buffer solution. The loading can be manual or automated. In one example, the loading can be done with a pipette. In some examples, the source can be retained in a buffer. The buffer solution utilized can vary depending on the source of the genetic material. For example, zebra fish can be retained in an E3 buffer solution.

In another example, the step of moving the abrasive surface relative to the living source can include oscillating the multiple reservoirs in a 1 mm to 5 mm diameter circular planar motion at 50 rotations per second (Hz) to 250 Hz. In yet another example, moving the abrasive surface relative to the living source comprises placing the multiple reservoirs on a 1 volt to 3 volt coin vibration motor and operating the coin vibration motor for 5 minutes to 15 minutes. In yet another example, the step of moving the abrasive surface relative to the living source can include sonication, or ultrasound, or rapid movement in a channel. Thus, the movement mechanism can include a sonic generator, an ultrasound transducer, a fluid pump, a vibration motor, or the like. In further examples, the step of moving can include any of the movement mechanisms described above.

Following collection, the recovered genetic material can be amplified to form an amplified genetic material or otherwise analyzed. In some examples, the method can further include amplifying and/or analyzing the recovered genetic material using polymerize chain reaction (PCR), gel electrophoresis, high-resolution melt analysis (HRMA), or a combination thereof. The recovered genetic material does not require DNA isolation prior to amplification and/or analysis. The analysis can occur with or without amplification. HRMA can be used to identify variations in DNA sequences as low as a single nucleotide by detecting minute differences in DNA denaturation at specific temperatures.

The method provided herein can be conducted by a single operator and can have a total DNA extraction time ranging from 20-30 minutes with a greater than 90% survival rate, in many cases greater than 95%, and in some cases greater than 99%. In one example, the process time process time to collect the genetic material from 48 of fewer of the living sources of the genetic material can be thirty minutes or less with a survival rate of the living source of genetic material of greater than 90%. In another example, a process time to collect the genetic material from 24 of fewer of the living sources of the genetic material can be twenty minutes or less with a survival rate of the living source of genetic material of greater than 85%. In some examples, the sensitivity of the device can be greater than 95% with survival rate of 100%. Process times can be less than 20 minutes for 16-24 embryos and less than 30 minutes for 48 embryos. In some examples, genotyping of 500 embryos with greater than 85% survivability of the genotyped embryos can occur in less than 5 hours.

The device and method presented herein can have the capacity to be multiplexed to allow the collection of DNA from multiple embryos simultaneously and can complete collection of genetic material from hundreds of embryos in a few hours with minimum operator involvement. Furthermore, the movement can be done in the absence of sonication.

In some examples, the method can be automated utilizing standard approaches. For example, a microprocessor, pressure/vacuum source with micropump controlled by a motor driver and an integrated circuit can be used to drive the direction of fluids containing embryos in a microarray containing chambers or channels. In yet another alternative, a benchtop robotic liquid handler can be utilized to automate movement of embryos/source or samples for higher throughput.

EXAMPLES

Example 1

Open Top Droplet Multi-Reservoir Array and Extraction

A standard glass microscope slide was utilized to generate a multi-reservoir array. Sixteen roughened patches 4 mm in diameter were etched onto the slide utilizing a $CO_2$ laser. The roughened patches had a surface roughness (Ra) of 2 μm. Double sided KAPTON tape approximately 100 microns thick was cut to the shape of the slide including holes 5 mm in diameter that substantially aligned with the roughened patches on the slide. The KAPTON tape was attached to the glass surface slide having the roughened patches centered through the holes in the KAPTON tape.

The multi-reservoir array, above, was then attached to a base unit consisting of an acrylic structure designed to hold the multi-reservoir array orthogonal to gravity. The base unit was designed to have minimal contact with the multi-reservoir array and allowed 1-2 mm of freedom of movement in the x direction and the y direction.

An 8 mm×3 mm cylindrical coin vibration motor was attached to the base unit with double sided tape. Each reservoir of the multi-reservoir array was manually loaded a 72 hour post fertilization (hpf) embryo with a 10-100 μL pipette from a solution including 72 hpf embryos in 15 μL of E3 buffer. The coin vibration motor was supplied with 1.4 volts of electricity for 10 minutes. A 1-10 μL pipette was utilized to collect fluid and the extracted genetic material from each of the reservoirs while taking care to avoid touching the embryo in each reservoir.

The collected fluid and extracted genetic material can then be used for genotyping, population monitoring, or other analysis. The embryos were then transferred from the multi-reservoir array to a standard 96 well plate for further use.

Example 2

Multiple Multi-Reservoir Arrays & Analysis

Three different multi-reservoir arrays were created with 20 μL PDMS molded article including holes that formed the side walls of the reservoirs which was adhered to a roughed glass slide. Multi-reservoir array 2 and 3 consisted of an open top droplet system as manufactured in Example 1 and tested. The chip includes or consists of a standard glass microscope slide that has a plurality (16-48) of roughened patches, currently circular and 4 mm in diameter, etched into the top surface of the glass slide using a $CO_2$ laser system. A double sided KAPTON tape of approximately 100 microns in thickness is cut to the shape of a standard microscope slide and includes through holes, currently 5 mm in diameter, that align to the roughened patches on the glass microscope slide. The KAPTON tape is aligned and attached to the glass surface creating open but shallow chambers wherein the roughened glass patches are centered in the through holes made in the KAPTON tape.

The base unit was an acrylic structure designed to hold the chip orthogonal to gravity, wherein the force of gravity is the negative z direction, such that the chip has freedom of movement (currently 1-2 mm) in the x and y directions of the z plane. The base unit is designed such that the structure has minimal physical contact with the chip.

The device was operated by first, manually loading the chip chambers using a standard single channel 10-100 microliter pipette and custom tip with embryos (72 hours post fertilization) each in 15 uL of E3 buffer. This process takes roughly 2 minutes for 16 embryos. Then, a cylindrical coin vibration motor roughly 8 mm in diameter and 3 mm in height (part number: xyz) is attached directly to the bottom side of the glass using double sided tape. Next, the chip is loaded into the base unit and the vibration motor is processed by supplying 1.4 volts to the motor for 10 minutes. Then, the chip is removed from the unit and a standard 1-10 microliter pipette was used to collect 10 uL of fluid from each chamber. This 10 microliter sample contains genetic material from the embryo. Care is taken to avoid touching the embryo with the pipette tip. Immediately following the removal of the sample, the embryo is transferred from the chip using a standard 2 mL disposable pipette to a standard 96-well plate. Fluid levels for each embryo were maintained at approximately 300 μL. The genetic material sample is genotyped using a standard PCR instrument (part number: xyz).

A test was designed to complete a screen of 500 zebrafish embryos in 4 hours. The test was completed by a team of 8 people. The team operated two systems which simultaneously processed 1 chip (16 embryos per chip) every 10 minutes. The entire test, including 1.5 hours of PCR/HRMA time only, was completed in 4 hours and 39 minutes. Of the 4 hours and 39 minutes, sample extractions for 500 embryos were completed in 3 hours and 28 minutes. Sensitivity and survivability were 72.3% and 87.9% respectively, both of which can be improved with additional optimization. This process can be readily automated, so a team of 8 people can be reduced to 1 person who only needs to briefly interact with the instrumentation.

The multi-reservoir array chip was loaded into a base unit. Embryos (72 hpf) were loaded into a chip chamber using a standard pipette with a wide bore tip. Cell extraction protocol was performed for 10 minutes (automated). Cell samples were collected using a standard pipette. The fish were relocated to a well plate using a disposable transfer pipette.

The gel was completed using DNA samples generated by the Zebrafish Embryo Genotype (ZEG) device on abcd1 splice variant (SNP) Zebrafish Embryos. The gel was completed using 72 hpf embryos (abcd1-zc90).

Figure 7A:
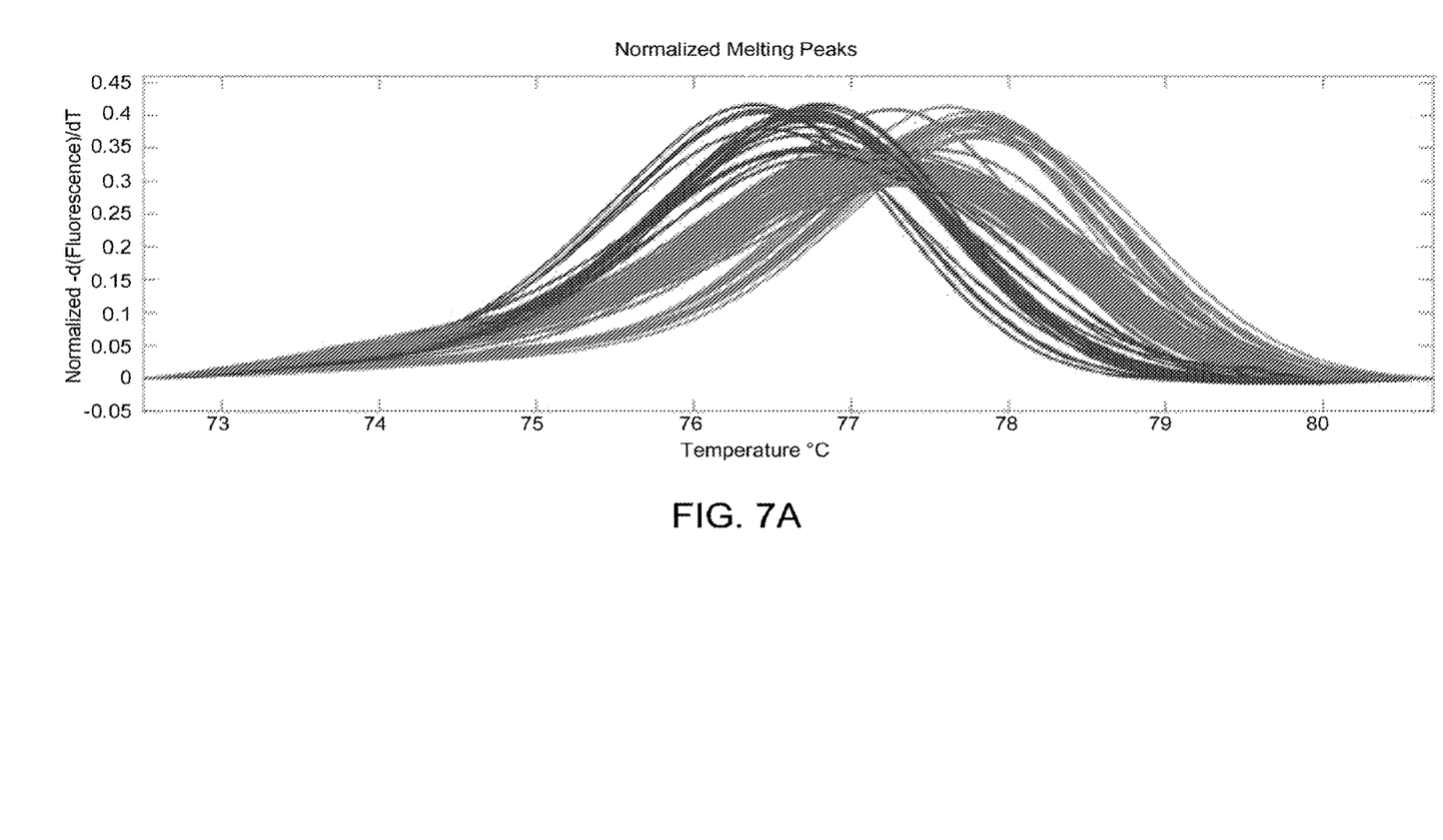
FIG. 7A-7C is a collection of data output for genotyping identification of embryos and transgenic offspring in accordance with an example presented herein.
Figure 7B:
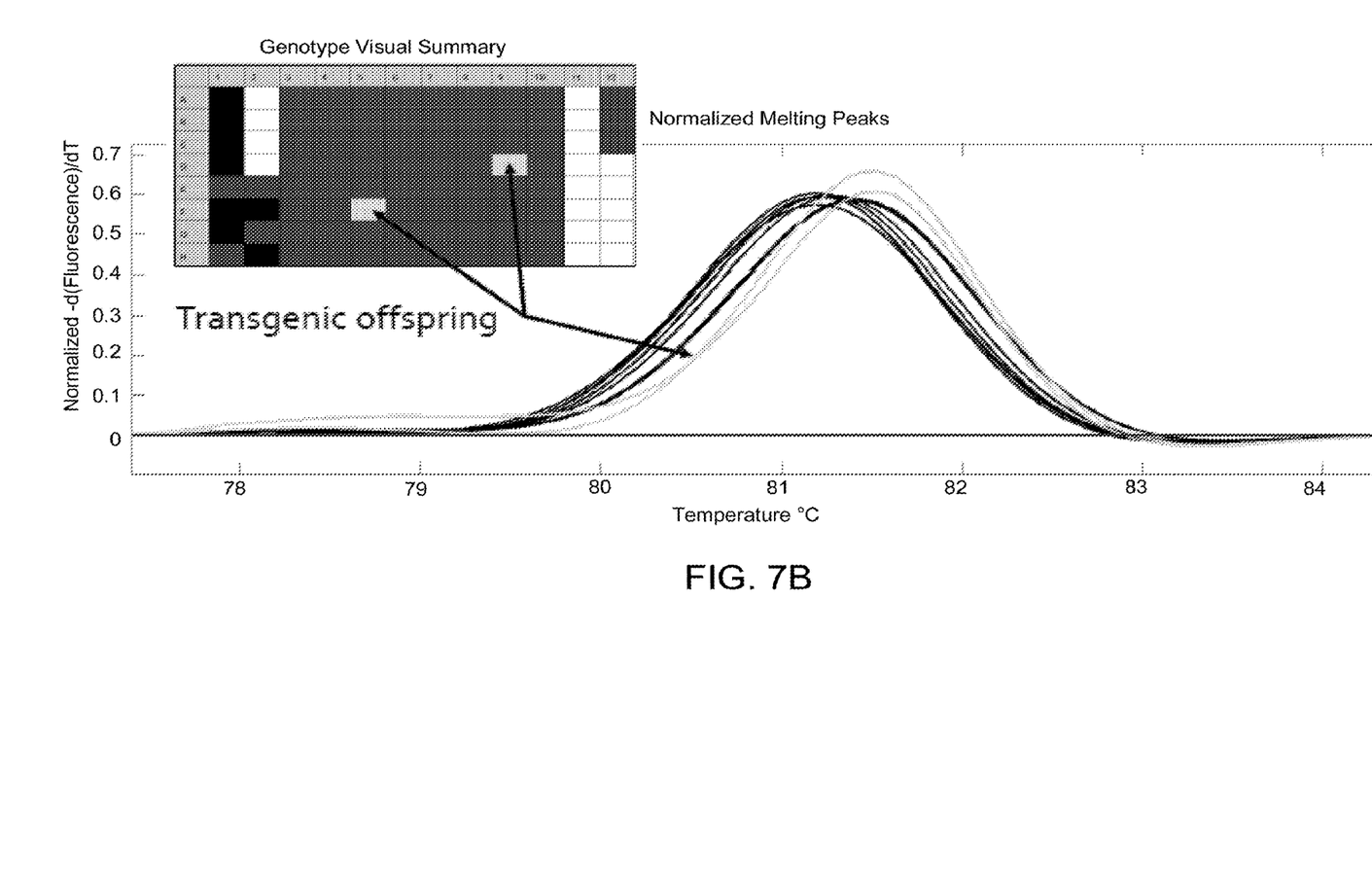

In FIG. 7A, an input of Founder outcross to wildtype (80 embryos—72 hpf) gave an output of genotyped embryos and transgenic offspring were identified. Time for DNA extraction, PCT and HRMA was about 2 hours. This approach has shown particular value in screening for founder transgenic fish. Rare transgenic offspring can also be determined at the embryonic stage without sacrificing embryos as shown in FIG. 7B.

Figure 7C:
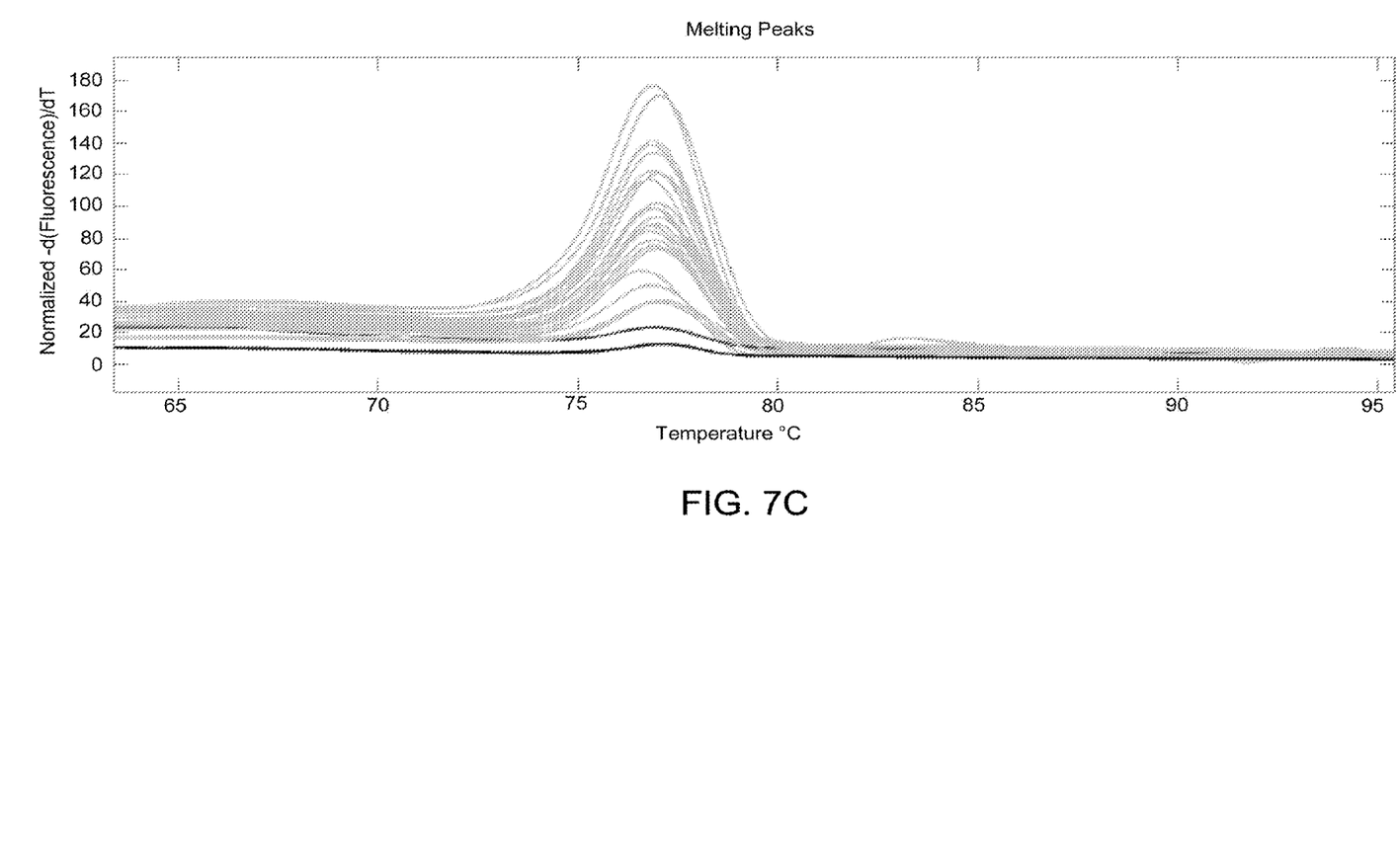

DNA was extracted from 504 live embryos in 3 hours and 28 minutes by a team of 6 people. The total time including genotyping using HRMA was 4 hours and 39 minutes. The HRMA plot of FIG. 7C shows melting peaks for embryos (abcd1-sa509) processed simultaneously on a single chip by a single user.

The device and method presented herein provide a framework for enhanced utilization of genetics and screening potential. In addition, this device and method can be an important resource for next-generation sequencing, with the abundance of untested gene variants and can provide a means to assay biological relevance. The device can provide at least three benefits: (1) embryos can be kept alive after genetic material collection and analysis, (2) genotyping can be performed early in the life cycle of the embryo, saving time and costs; and (3) the processes can be automated and can be efficient for high-throughput studies.

Figure 8A:
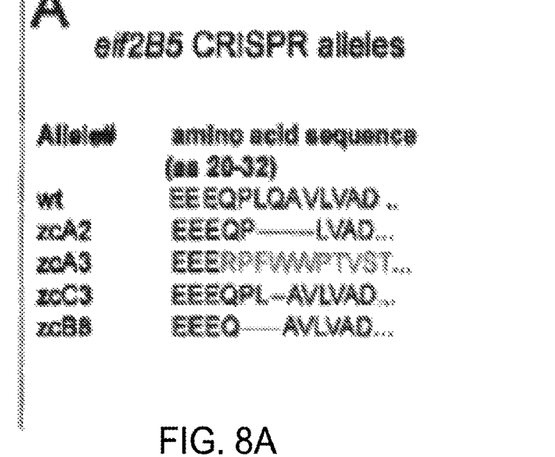
FIG. 8A lists CRISPR mutant alleles, in accordance with an example presented herein.
Figure 8B:
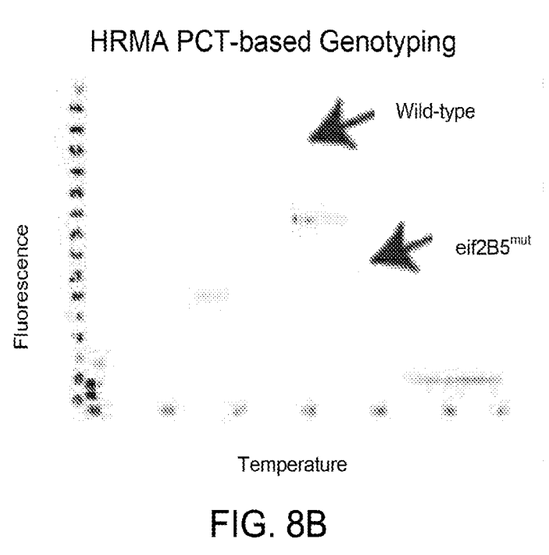
FIG. 8B shows HRMA PCR detection of mutant alleles in accordance with an example presented herein.
Figure 8C:
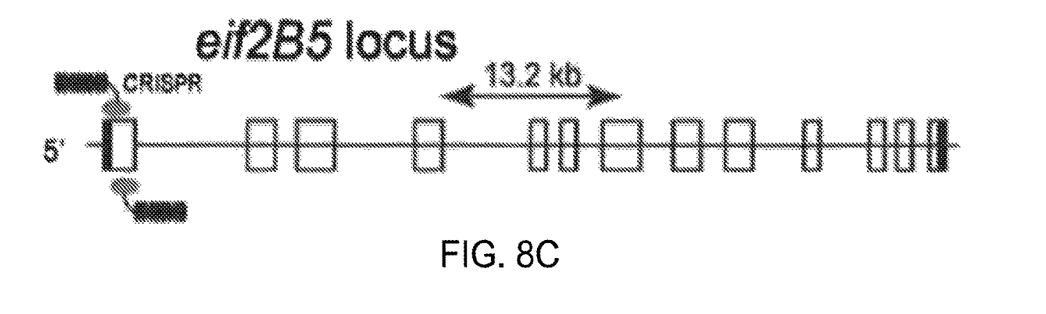
FIG. 8C is an eif285m CRISPR line in accordance with an example presented herein.

Mutants in the zebrafish eif2B5 gene were prepared. A rapid screening method was developed based on melt-curve analysis to identify mutants (FIG. 8A-C). The eif285m line (the line carrying the mutation in the eif2B5 gene) is heterozygous viable and fertile, but the homozygous mutants, although surviving to adulthood, are not fertile. The microfluidic device can be used at two steps: 1) genotyping and sorting of animals into known genotypes. Animals of known genotypes can be used for phenotypic characterization and for raising to the next generation. 2) Sorting of heterozygous in-crosses to obtain homozygous mutants to use in a therapeutic compound screen. Thus, known homozygotes can be obtained to use in a screen. Wild-types, heterozygotes, and homozygotes can be distinguished of at least two different mutant alleles. Different mutation types identified by HRMA can also be confirmed by cloning and sequencing of PCR products.

Each of the multi-reservoir arrays was manually loaded using a standard single channel pipette and custom tip with 16 embryos each in 15 µL of E3 buffer. This process took roughly 2 minutes. Multi-reservoir array 1 was placed on a shaker plate and shaken at 100 rpm for 10 minutes. Multi-reservoir arrays 2 and 3 were placed on a 10 mm coin vibration motor operated at 2 volts and oscillated for 10 minutes. Then, a standard pipette was used to collect 10 µL of fluid from each reservoir of the multi-reservoir arrays. The sensitivity, survival rate, number of embryos, and total time for the extraction are all tabulated below.

TABLE 1

| Microarray | Sensitivity | Survival | Time | Embryos (n) |
|---|---|---|---|---|
| 1 | 51% | 81% | 1 hr 15 min (extraction only) | 96 |
| 2 | 93.75% | 93.75% | 45 min (extraction only) | 48 |
| 3 | 72.3% | 87.9% | 4 hr 39 min (extraction and genotyping) | 500 |

The extracted genetic material from microarray 3 was further screened and genotyped. The team of eight individuals completed the screening of 500 zebrafish embryos in 4 hours. The team operated two systems which simultaneously processed one microarray (16 embryos per microarray) every 10 minutes. The entire test, including 1.5 hours of PCR/HRMA time, was completed in 4 hours and 39 minutes; sample extractions for 500 embryos were completed in 3 hours and 28 minutes. Sensitivity and survivability were 72.3% and 87.9% respectively. The process can be readily automated, so a team of eight people can be reduced to a single individual who only needs to briefly interact with the instrumentation.

Example 3

Survivability Testing

Following extraction of the genetic material using an open top droplet system as described above, three different forms of analysis were tested. First, the ability of the multi-reservoir array and subsequent PCR was tested to reliably detect and differentiate three different alleles of a splice-site nucleotide change mutation in the gene abcd1. Following extraction, PCR, and HRMA, we were able to reliably distinguish wild-type, homozygous mutant, and heterozygous embryonic zebrafish.

Then, the extracted genetic material was analyzed to determine if sufficient amounts of DNA were present for PCR to be analyzed by agarose gel electrophoresis. The offspring were genotyped from crosses of three different mosaic founder adult zebrafish to wild-types, for a total of 74 embryos. The mosaic adults, each carried a Gal4-VP16 transgene, had been generated by Tol2-based transgenesis, and were previously determined as mosaic founders by sacrificing and genotyping their offspring. The extracted genetic material was amplified, visualized, and used to genotype with agarose gel electrophoresis. All of the embryos survived the genotyping and were able to support raising only the Gal4-VP16 transgenic offspring to adulthood.

The amplified DNA was of sufficient quality for sequencing. Embryos were genotyped from a cross of abcd1$^{zc90}$ heterozygous adults, carrying a 12-bp insertion. Following extraction, PCR, and sequencing, more than 260 bp of readable sequence were obtained and could distinguish wild-type, heterozygous, and homozygous mutant embryo sequences.

Finally, embryos were tested to confirm correct genotyping. Transgenic animals were crossed to wild-type animals. Transgenic embryos carried a visible marker, GFP expressed under the control of a cardiac promoter, in the line Tg(myl7: EGFP; foxP2-enhancerA.2:Gal4-VP16$_{413-470}$)$^{zc72}$, in which the Gal4-containing transgene was stably integrated into the genome together with GFP. GFP-negative, wild-type embryos did not have PCR amplification of the Gal4 amplicon; but all GFP-positive embryos carrying the Gal4 transgene were successfully amplified After genotyping, the survival rate was 100% (n=96 embryos); and there were no differences in gross body morphology of visually inspected larvae from 3 days post fertilization (dpf) through 7 dpf. Further, animals that were raised to adulthood (>3 months) had no apparent effects on long-term growth or development and were fertile. Behavior was tested at 7 dpf following chip genotyping at 3 dpf. Spontaneous, light-evoked, and tap-evoked swimming behavior was performed, and no differences were found between microarray-run larvae (n=36) and control larvae (n=48) from the same clutch in total distance swam (p=0.88, 0.53, 0.64 respectively; Student's t-test) or time spent moving (p=0.38, 0.52, 0.78 respectively).

The embryos were unharmed, with no apparent adverse effects on survival, morphology, or behavior, and can be used for subsequent experiments or raised to adulthood. The device provided cells and DNA that can be used for PCR-based applications including gel electrophoresis, sequencing, and HRMA. The cells can also provide RNA or protein for analysis, although the quantities will be low and can be primarily epidermal in origin.

Example 4

Cross-Contamination Testing

The open top droplet multi-reservoir array was analyzed for the potential for cross-contamination between individual reservoirs on the multi-reservoir array. A multi-reservoir array as described in Example 1 was created having 16 reservoirs. Eight of the reservoirs were loaded with embryos in 10 μL of an E3 solution and the alternating 8 other reservoirs were loaded with 10 μL of an E3 solution. Extraction was carried out as described earlier and samples/embryos were collected. All 8 embryos were successfully genotyped and no cross-contamination was observed.

Example 5

Further Chip Construction & Testing

Extraction chips were made from standard glass microscope slides. Circular roughened patches were etched into the top surface of the glass slide using a $CO_2$ laser system (Universal Laser Systems VLS 3.60). Double sided polyimide tape was cut to the glass slide dimensions; circular holes were cut in the same configuration as the roughened patches made by the laser. The polyimide tape was aligned and attached to the glass surface creating open but shallow chambers wherein the roughened glass patches are centered in the through holes made in the polyimide tape. Chips having 16, 24, and 48 chambers were made as in Example 1.

DNA was then collected for PCR to be analyzed by agarose gel electrophoresis. Agarose gel electrophoresis is considered less sensitive than HRMA and is less commonly available. The offspring were genotyped from crosses of three different mosaic founder adult zebrafish to wild-types, a total of 74 embryos. The mosaic adults, each of which carried a Gal4-VP16 transgene, had been generated by Tol2-based transgenesis, and were previously determined as mosaic founders by sacrificing and genotyping their offspring. The genetic material was amplified from the collection system and could be visualized and used to genotype with agarose gel electrophoresis. Further, all of the embryos survived the genotyping, and were able to support raising only the Gal4-VP16 transgenic offspring to adulthood. This approach saved effort and cost by raising only the desired genotype, and by-passing the requirement for fin-clip genotyping of the adults.

The amplified DNA from the collection system was of sufficient quality for sequencing. Specifically, embryos were genotyped from a cross of abcd1$^{zc90}$ heterozygous adults, carrying a 12-bp insertion. Following extraction, PCR, and sequencing, more than 260 bp of readable sequence were obtained and could distinguish wild-type, heterozygous, and homozygous mutant embryo sequences.

Finally, embryos were tested to confirm correct genotyping. For this experiment, transgenic animals were crossed to wild-type animals. Transgenic embryos carried a visible marker, GFP expressed under the control of a cardiac promoter, in the line Tg(myl7:EGFP; foxP2-enhancerA.2:Gal4-VP16$_{413-470}$)$^{zc72}$ (Stevenson et al., 2012), in which the Gal4-containing transgene is stably integrated into the genome together with GFP (Kwan et al., 2007). GFP-negative, wild-type embryos did not have PCR amplification of the Gal4 amplicon; but all GFP-positive embryos carrying the Gal4 transgene successfully amplified After genotyping with the collection device survival was 100% (n=96 embryos); and there were no differences in gross body morphology. Visual inspection was performed of larvae from 3 through 7 dpf. Further, animals that were raised to adulthood (>3 months) had no apparent effects on long-term growth or development and were fertile.

Behavior was tested at 7 dpf following chip genotyping at 3 dpf. Spontaneous, light-evoked, and tap-evoked swimming behavior was performed, and no differences were found between chip-run larvae (n=36) and control larvae (n=48) from the same clutch in total distance swam (p=0.88, 0.53, 0.64 respectively; Student's t-test) or time spent moving (p=0.38, 0.52, 0.78 respectively).

These example systems and methods use harmonic oscillation of embryos over a roughened glass surface to obtain genetic material that can be directly used for genotyping. The embryos were unharmed, with no apparent adverse effects on survival, morphology, or behavior, and can be used for subsequent experiments or raised to adulthood. The system was tested for embryos older than 48 hpf that are out of their chorions; and up through age ~96 hpf larvae. The system provided cells and DNA that can be used for PCR-based applications including gel electrophoresis, sequencing, and HRMA. The cells can also provide RNA or protein for analysis, although the quantities may be low and can be primarily epidermal in origin.

The system can genotype live embryos and larvae, a process for mutant screens, maintenance of zebrafish stocks, and for use in drug or behavioral testing. The system also allows researchers to identify and raise mutants of interest at an early stage of zebrafish development rather than having to wait until maturity at age two to three months. Further, this system can be used to identify homozygous, heterozygous, and wild-type embryos for a given genotype or mutation, allowing characterization of embryonic phenotypes and responses while the animals are alive.

Optionally, the system may be fully automated for loading and unloading. Further, for example, the chip can be integrated such that the collected fluid can be analyzed directly, by performing the PCR on the chip. Other options include target expanding the developmental age of embryos and larvae that the device can genotype.

The foregoing detailed description describes the invention with reference to specific exemplary embodiments. However, it will be appreciated that various modifications and changes can be made without departing from the scope of the present invention as set forth in the appended claims. The detailed description and accompanying figures are to be regarded as merely illustrative, rather than as restrictive, and all such modifications or changes, if any, are intended to fall within the scope of the present invention as described and set forth herein.

What is claimed is:
1. A device for rapid non-destructive genetic material collection, comprising:
   a multi-reservoir array including multiple reservoirs, wherein a plurality of the multiple reservoirs, include an abrasive surface, capable of retaining a source of genetic material in a liquid carrier wherein the abrasive surface has a roughness; and a movement mechanism configured to move the multi-reservoir array in an oscillating motion, and thereby configured to create relative movement between the abrasive surface and the source of the genetic material in order to remove a portion of genetic material from the source of the genetic material without destroying the source of the genetic material or the portion of the genetic material that is removed.

2. The device of claim 1, wherein the multi-reservoir array comprises an open top droplet system wherein the multiple reservoirs are formed having a reservoir bottom, reservoir side wall, and an open top to allow access to the multiple reservoirs.

3. The device of claim 2, wherein the multi-reservoir array comprises a slide forming the reservoir bottom, a hydrophobic tape with holes that form the reservoir side walls, and the abrasive surface comprises a roughened surface on the slide.

4. The device of claim 2, wherein the reservoir side wall comprises a molded polydimethylsiloxane (PDMS) and the molded PDMS is adhered to a slide.

5. The device of claim 1, wherein the multi-reservoir array comprises up to 96 reservoirs and the reservoirs are circular with a diameter ranging from 2 mm to 8 mm in size.

6. The device of claim 1, wherein the abrasive surface comprises a member selected from the group consisting of a roughened portion of the multiple reservoirs, an abrasive material attached to an interior surface of the multiple reservoirs, and a combination thereof.

7. The device of claim 1, wherein the abrasive surface is located along a bottom of the multiple reservoirs, a side wall of the multiple reservoirs, or a combination thereof.

8. The device of claim 1, wherein the roughness (Ra) and a surface waviness (Wa) ranges from 1 µm to 100 µm.

9. The device of claim 1, wherein the movement mechanism comprises a member selected from the group consisting of a shaker plate, an orbital shaker, a linear shaker, a rocking shaker, a gyratory rocker, a micro-plate mixer, a vibration motor, a coin vibration motor, a reciprocating rack, a sonic generator, an ultrasound transducer, a pump, and a combination thereof.

10. The device of claim 1, wherein the movement mechanism is located along a bottom surface of the multi-reservoir array.

11. The device of claim 1, wherein the movement mechanism is located adjacent a lateral edge of the multi-reservoir array.

12. A method of rapid non-destructive genetic material collection; comprising:
retaining an living source of genetic material within multiple reservoirs having an abrasive surface therein;
moving the abrasive surface relative to the living source of the genetic material in a manner that removes genetic material from the source of the genetic material without destroying the genetic material and the living source of the genetic material to form a recovered genetic material; and
collecting the recovered genetic material.

13. The method of claim 12, wherein the living source of genetic material comprises a 24-96 hour post fertilization embryo.

14. The method of claim 12, wherein a species of the living source of genetic material is *Danio rerio, drosophila*, nematode, *C. elegans*, or *xenopus*.

15. The method of claim 12, wherein retaining the living source of genetic material within the multiple reservoirs comprises loading the reservoirs with a 10 µL to 20 µL buffer solution containing the living source of the genetic material.

16. The method of claim 12, wherein moving the abrasive surface relative to the living source comprises oscillating the multiple reservoirs in a 1 mm to 5 mm diameter circular planar motion at 50 rotations per second (Hz) to 250 Hz.

17. The method of claim 12, wherein moving the abrasive surface relative to the living source comprises placing the multiple reservoirs on a 1 volt to 3 volt coin vibration motor and operating the coin vibration motor for a period of time ranging from 5 minutes to 15 minutes.

18. The method of claim 12, wherein the method further comprises amplifying the recovered genetic material using polymerize chain reaction (PCR) to form amplified genetic material.

19. The method of claim 18, wherein the method further comprises analyzing the amplified genetic material using a technique selected from the group consisting of gel electrophoresis, high resolution melt analysis, and a combination thereof.

20. The method of claim 11, wherein a process time to collect the genetic material from 48 or fewer of the living source of the genetic material is thirty minutes or less with a survival rate of the living source of genetic material of greater than 90%.

21. The method of claim 11, wherein a process time to collect the genetic material from 24 or fewer of the living source of the genetic material is twenty minutes or less with a survival rate of the living source of genetic material of greater than 90%.

* * * * *